United States Patent [19]
Shigetou et al.

[11] Patent Number: 5,922,618
[45] Date of Patent: Jul. 13, 1999

[54] DYE-LABELED ANTIBODY CONJUGATE AND PREPARATION METHOD THEREOF

[75] Inventors: Nobuyuki Shigetou; Jinsei Miyazaki; Mahito Hirai, all of Osaka, Japan

[73] Assignee: Matsushita Electric Industrial Co., Ltd., Osaka, Japan

[21] Appl. No.: 08/831,204

[22] Filed: Apr. 2, 1997

[30] Foreign Application Priority Data

Mar. 4, 1996 [JP] Japan .................................. 8-081246

[51] Int. Cl.$^6$ ........................ G01N 33/549; C07K 16/00
[52] U.S. Cl. ........................... 436/532; 436/800; 435/7.1; 530/387.1; 524/900; 424/1.49
[58] Field of Search ........................ 530/387.1; 436/800, 436/532; 435/7.1; 524/900; 424/1.49

[56] References Cited

U.S. PATENT DOCUMENTS 4,069,352  1/1978  Parsons ........................................ 427/2

FOREIGN PATENT DOCUMENTS

| 0175560 | 3/1986 | European Pat. Off. ..... G01N 33/535 |
| 0 609 894 | 8/1994 | European Pat. Off. . |
| 9568273 | 10/1996 | Japan .............................. C09B 23/00 |
| WO 90/09196 | 8/1990 | WIPO . |
| WO 92/15882 | 9/1992 | WIPO . |

OTHER PUBLICATIONS

Mar. 1998, Communication from European Patent Office and attached Search Report.

Mujumdar, et al., "Cyanine Dye Labeling Reagents: Sulfoindocyanine Succinimidyl Esters", *Bioconjugate Chemistry*, vol. 4, No. 2, Mar./Apr. 1993, pp. 105–111.

Staros (1982) Membrane impermeant cleavable cross–linkers, Biophys. J., vol. 37, pp. 21–22.

*Primary Examiner*—Lynette F. Smith
*Assistant Examiner*—Ali R. Salimi
*Attorney, Agent, or Firm*—Merchant, Gould, Smith, Edell, Welter & Schmidt

[57] ABSTRACT

The invention relates to a dye-labeled antibody conjugate comprising an antibody conjugate and a cyanine dye. The dye-labeled antibody conjugate is prepared by polymerizing an antibody such as mouse IgG in phosphate buffer using a polyfunctional reagent such as dithiobis (sulfosuccinimidylpropionate), and stirring the antibody and a cyanine dye represented by Formula I . The dye-labeled antibody conjugate is more sensitive to antigens than conventional dye-labeled antibodies because it has many reactive sites to antigens.

Formula I

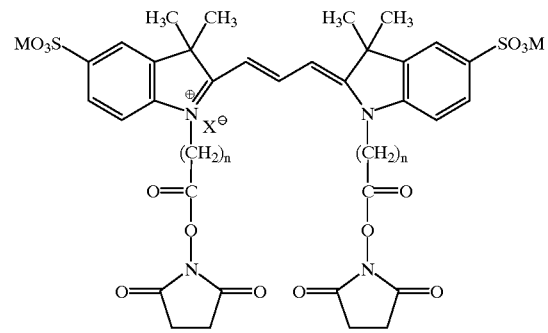

wherein X represents a halogen, M represents a hydrogen or alkali metal, and n represents an integer of 1 to 4

8 Claims, 1 Drawing Sheet

DYE-LABELED ANTIBODY CONJUGATE AND PREPARATION METHOD THEREOF

FIELD OF THE INVENTION

The invention relates to an antibody conjugate labeled with a cyanine dye and to a method of preparing the antibody conjugate.

BACKGROUND OF THE INVENTION

Dye-labeled antibodies have been used in analysis such as immunochromatography because of their reactive specificity. Cyanine dyes having reactive functional groups are often used as a dye to label antibodies (Bioconjugate Chemistry, VOL. 4, No. 2, pp105–111, 1993). The functional groups in the cyanine dyes bond to amino or carboxy groups of the antibodies to form covalent bonds. Twenty to fifty molecules of the dye bond to one molecule of an antibody. The dye-labeled antibodies thus prepared are generally easy to recognize with the naked eye. Such dye-labeled antibodies are used in immunochromatography, for example, to detect a trace of some components like human chorionic gonadotropin (hCG), which is present only in urine from pregnant women.

However, the conventional dye-labeled antibodies had a limited capability in detection for some antigens. A low concentration of substances to be detected rendered the detection difficult.

SUMMARY OF THE INVENTION

To solve the above-noted problems, the invention provides a more sensitive dye-labeled antibody conjugate which detects even a low concentration of intended substances.

A first aspect of the invention is a dye-labeled antibody conjugate comprising an antibody conjugate and a cyanine dye, wherein the antibody conjugate comprises an antibody polymerized using a polyfunctional reagent, and the antibody conjugate is labeled with the cyanine dye. Conventional dye-labeled antibodies had a limited sensitivity for a satisfactory detection because they only had 2 sites to bond to antigens. On the contrary, the dye-labeled antibody conjugate of the invention is extremely excellent in sensitivity because the antibody conjugate comprises polymerized antibodies, having many reactive sites to antigens. Therefore, when the dye-labeled antibody conjugate of the invention is applied to immunochromatography, the dye-labeled antibody conjugate detects even a low concentration of intended substances with high sensitivity. Further, the dye-labeled antibody conjugate of the invention is suitable for biosensors.

The kind of antibodies applicable for this invention are not particularly limited. Independently of their origin or subclass, any antibodies are useful. Examples of preferred antibodies, i.e. immunoglobulin (Ig), include mouse IgG, mouse IgM, mouse IgA, mouse IgE, rat IgG, rat IgM, rabbit IgG, rabbit IgM, goat IgG, goat IgM, sheep IgG and sheep IgM. Such antibodies can be either commercially available or collected directly from such animals.

In the first aspect of the invention, it is preferable that the polyfunctional reagent is dithiobis(sulfosuccinimidylpropionate)(referred to as DTSSP).

In the first aspect of the invention, it is preferable that the cyanine dye is a cyanine dye having a chemical structure represented by Formula I

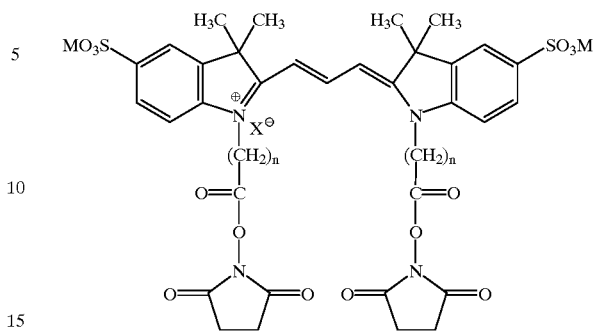

Formula I wherein X represents a halogen, M represents a hydrogen or alkali metal, and n represents an integer of 1 to 4

Red dyes are easy to recognize with the naked eyes. When machinery such as sensors is used in detecting, dyes other than red ones are also useful.

Examples of the halogen represented by X in Formula I include fluorine, chlorine, bromine and iodine. Examples of the metal represented by M include lithium, sodium and potassium.

In the first aspect of the invention, it is preferable that the antibody conjugate is bonded to a dye-skeleton of the cyanine dye via a covalent bond. The covalent bond is typically a covalent bond between succinimidyl groups of the cyanine dye and amino groups of the antibody.

The dye-labeled antibody conjugate of the invention usually has a polymerization degree from 2 to 50.

A second aspect of the invention is a method of preparing a dye-labeled antibody conjugate comprising the steps of polymerizing antibody using a polyfunctional reagent in the presence of a buffer having a pH value in a medium or slight alkaline region and adding a cyanine dye to the buffer in order to label the polymerized antibody. Phosphate buffer solution (PBS) is an example of a preferred buffer. The pH value of the buffer usually ranges from 7.0 to 8.0.

DETAILED DESCRIPTION OF THE INVENTION

Figure 1:
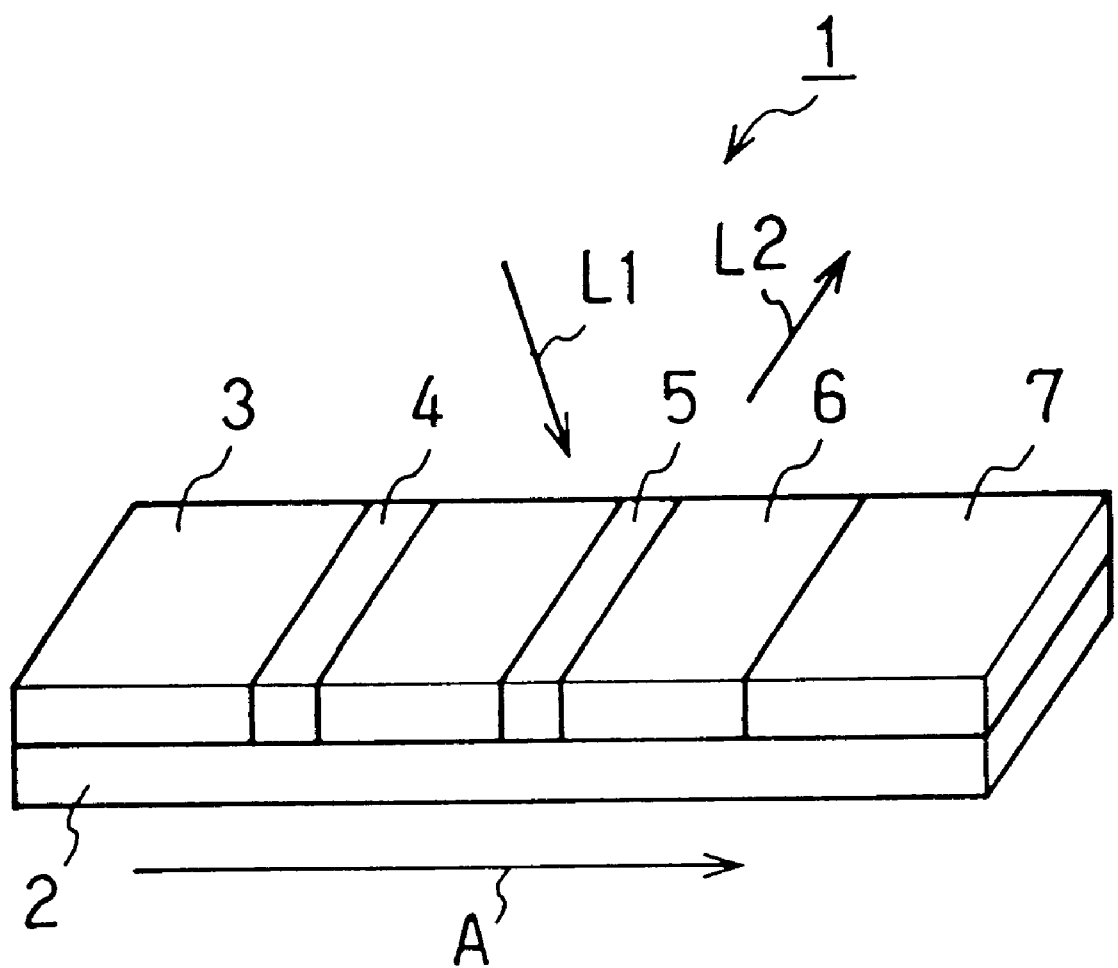
FIG. 1 is a perspective view of an example of an immunochromatographic sensor for the embodiment of the invention.

The cyanine dye used in the invention is prepared, for example, by dissolving a carboxylic acid derivative represented by Formula II in an organic solvent and then stirring the mixture together with hydroxysuccinimide.

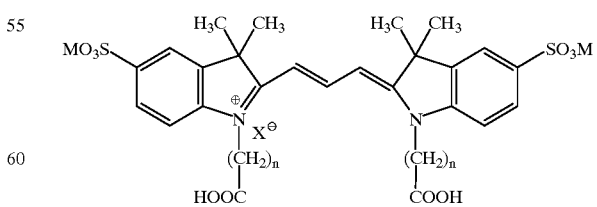

Formula II wherein X represents a halogen, M represents a hydrogen or alkali metal, and n represents an integer of 1 to 4

Formula III shows an example of the reaction scheme for synthesizing the cyanine dye represented by Formula I.

Formula III

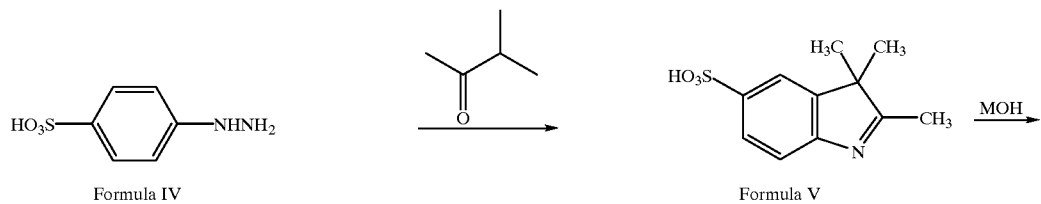

Formula IV → Formula V

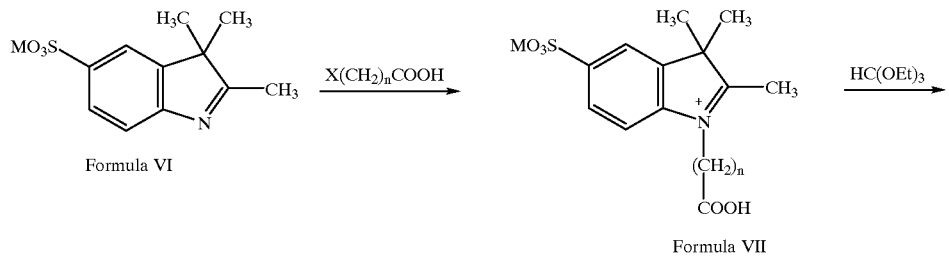

Formula VI → Formula VII

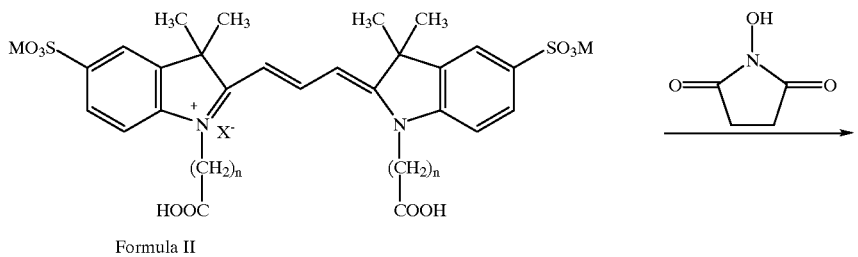

Formula II

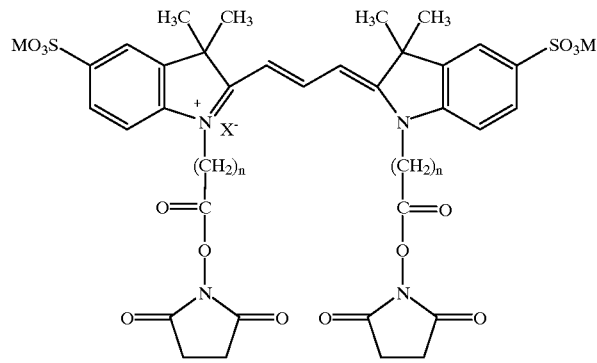

Formula I

The synthesis shown in Formula III will be explained below. Indolenium sulfonate represented by Formula V is prepared by dissolving hydrazinobenzene sulfonic acid represented by Formula IV and isopropyl methyl ketone in a molar ratio of 0.5 to 2 in an acidic solvent such as acetic acid and heating the mixture at about 70 to 130° C. for 1 to 5 hours.

Formula IV

-continued

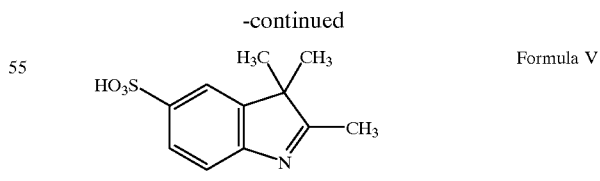

Formula V

A metal salt of indolenium sulfonate, represented by Formula VI, is prepared by mixing an alcoholic solution, for example, methanol solution, of indolenium sulfonate represented by Formula V and isopropyl alcohol which has been saturated with potassium oxide to form the potassium salt of indolenium sulfonate.

Formula VI

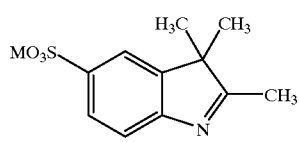

wherein M represents a hydrogen or alkali metal

A metal salt of a carboxyalkyl indolenium sulfonate, represented by Formula VII, is prepared by mixing a metal salt represented by Formula VI, for example, the potassium salt, and an equimolar amount of a halogenated alkyl acid such as iodopropionic acid in an organic solvent such as o-dichlorobenzene and then heating the mixture at about 80 to 130° C. for 2 to 12 hours to form the potassium salt of carboxyethyl indolenium sulfonate. The halogenated alkyl acid preferably has 1 to 4 carbon atoms in view of solubility in water. Iodopropionic acid, which has 3 carbon atoms, is suitable because it is water-soluble and easily reacts with indolenin.

Formula VII

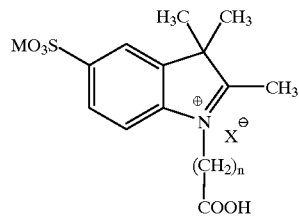

wherein X represents a halogen, M represents a hydrogen or alkali metal, and n represents an integer of 1 to 4

A carboxylic acid derivative represented by Formula II is prepared by dissolving a metal salt represented by Formula VII, for example, the potassium salt of carboxyethyl indolenium sulfonate, and ethyl orthoformate in a molar ratio of 0.5 to 2 in a basic organic solvent such as pyridine and heating the mixture at about 80 to 120° C. for 1 to 3 hours to form a propionic acid derivative.

A cyanine dye represented by Formula I is prepared by mixing a carboxylic acid derivative represented by Formula II, hydroxysuccinimide in a molar ratio of 0.5 to 2 and dicyclohexylcarbodiimide in a molar ratio of 0.5 to 2 as a condensing agent in an organic solvent solution, for example, dimethylformamide solution, and then stirring the mixture for 2 to 12 hours.

Examples of the halogen in Formulas I, II and VII include fluorine, chlorine, bromine and iodine. Examples of the metal salt in Formulas I, II, VI and VII include lithium salts, sodium salts and potassium salts.

Polyfunctional reagents applicable to the invention can be a reagent having at least two functional groups, each of which groups bonds to protein, in one molecule. Succinimidylester group is an example of such functional groups. In addition to DTSSP, examples of the polyfunctional agent for the invention include bis(sulfosuccinimidyl)suberate (BS$^3$) represented by Formula VIII, disuccinimidyltartrate (DST) represented by Formula IX, ethyleneglycolbis (succinimidylsuccinate) (EGS) represented by Formula X, and N-succinimidyl-3-(2-pyridyldithio)propiorate (SPDP) represented by Formula XI.

Formula VIII

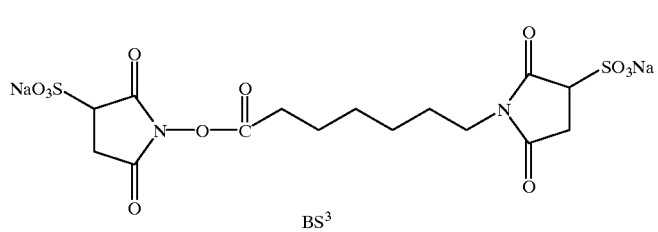

BS$^3$

Formula IX

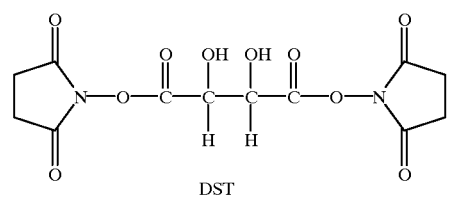

DST

Formula X

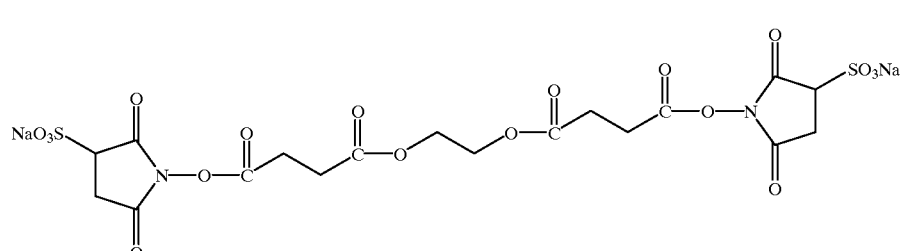

EGS

-continued

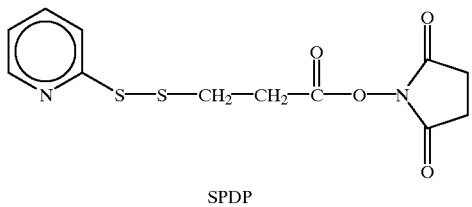

SPDP

The polymerization of antibodies using a reagent having at least two succinimidylester groups will be explained with reference to Formulas XII through XV.

Formula XII shows that a reagent having at least two succinimidylester groups is mixed with an antibody. Formula XIII shows that an amino group of the antibody comes close to an ester bonding site of one of the succinimidylester groups.

polymerizing agent

Formula XII

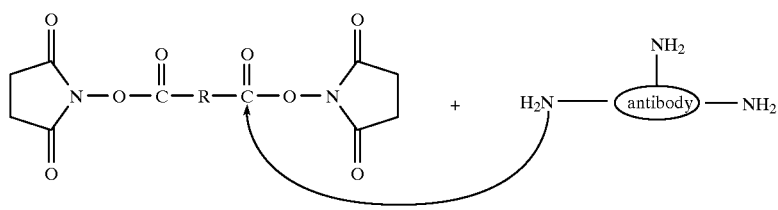

Formula XIII

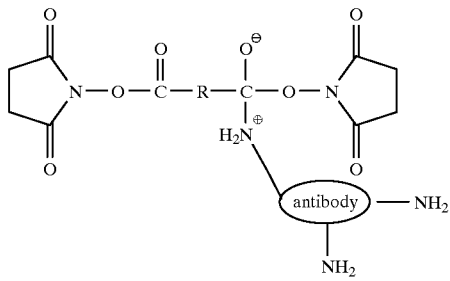

As shown in Formula XIV, the amino group of the antibody reacts with the ester bonding site of the succinimidylester group. One hydrogen atom is, consequently, taken away from the amino group, and then, succinimide is eliminated from the succinimidylester group. As a result, the succinimide together the hydrogen atom forms hydroxysuccinimide. At the same time, the residue of the succinimidylester group and the residue of the amino group, which has lost its hydrogen atom, form an amide bonding. Finally, the reagent bonds to the antibody via the amide bonding.

Formula XI

Formula XIV

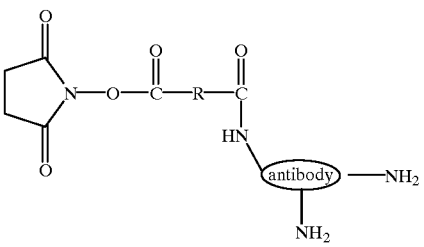

-continued

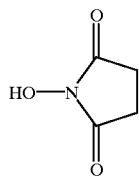

hydroxysuccinimide

Formula XV shows that another antibody similarly bonds to the other succinimidylester group via an amide bonding, because the above reaction also occurs to the other succinimidylester group. This reaction takes place in sequence so that antibodies are polymerized.

Formula XV

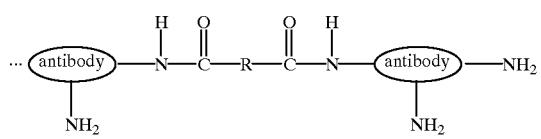

The dye-labeled antibody conjugate of the invention is prepared, for example, by dissolving mouse IgG in PBS, adding to the solution DTSSP in a molar ratio of 100 with respect to mouse IgG, polymerizing the mouse IgG, adding to the mixture a PBS solution of a cyanine dye represented by Formula I and then stirring the entire mixture at 4 to 30° C. overnight.

Embodiments of the invention will be presented. In this context, X and M in Formulas I, II, VI and VII are iodine and potassium, respectively, and n is 2. The antigen used was mouse IgG.

(1) Synthesis of Cyanine Dye

The cyanine dye represented by Formula I was synthesized through the course of the reaction shown in Formula III as follows.

① Synthesis of Indolenium Sulfonate

Hydrazinobenzene sulfonic acid, 10 g (53 mmol), and isopropyl methyl ketone, 16.8 ml (160 mmol), were dissolved in 30 ml of acetic acid, followed by a 3-hour reflux. After the reaction mixture was cooled to 0° C. and allowed to stand for 1 hour, the resulting solid was collected by filtration. The collected solid was washed twice with ether and dried under reduced pressure to form 11.8 g of indolenium sulfonate. The yield was 93%. Table 1 shows the structure of indolenium sulfonate, chemical shifts of NMR in dimethylsulfoxide (DMSO) and assignment of each peak.

TABLE 1

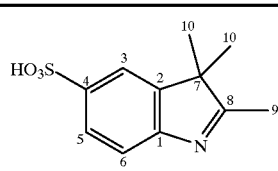

| Chemical Shift (δ, ppm) | Number of Hydrogen | Number of Peak | Assigned Carbon No. |
|---|---|---|---|
| 1.30 | 6 | 1 | 10 |
| 2.32 | 3 | 1 | 9 |
| 7.39 | 1 | 2 | 6 |

TABLE 1-continued

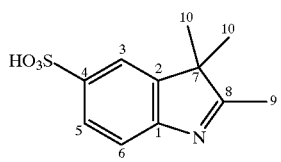

| Chemical Shift (δ, ppm) | Number of Hydrogen | Number of Peak | Assigned Carbon No. |
|---|---|---|---|
| 7.59 | 1 | 4 | 5 |
| 7.70 | 1 | 2 | 3 |

② Synthesis of Potassium Salt of Indolenium Sulfonate

Indolenium sulfonate, 11.8 g (49 mmol), which was synthesized in the manner as described in the above item ①, was dissolved in 20 ml of methanol. To the mixture was added about 300 ml of isopropyl alcohol saturated with potassium oxide, followed by stirring. The resulting pale yellow solid was collected by filtration. The collected solid was washed twice with isopropyl alcohol, and dried under reduced pressure to form 7.4 g of potassium salt of indolenium sulfonate. The yield was 55%. Table 2 shows the structure of the potassium salt, chemical shifts of NMR in dimethylsulfoxide (DMSO) and assignment of each peak.

TABLE 2

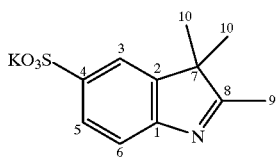

| Chemical Shift (δ, ppm) | Number of Hydrogen | Number of Peak | Assigned Carbon No. |
|---|---|---|---|
| 1.24 | 6 | 1 | 10 |
| 2.21 | 3 | 1 | 9 |
| 7.33 | 1 | 2 | 6 |
| 7.53 | 1 | 4 | 5 |
| 7.62 | 1 | 2 | 3 |

③ Synthesis of Potassium Salt of Carboxyethyl Indolenium Sulfonate

Potassium salt of indolenium sulfonate, 5.5 g (20 mmol), which was synthesized in the manner as described in the above item ②, and iodopropionic acid, 5 g (25 mmol) were suspended in 50 ml of orthodichlorobenzene. The suspension was stirred in an argon flow at 110° C. for 12 hours. In the early stage of the reaction at the temperature, the suspension was dissolved to a solution in about 30 minutes. After the 12-hour stirring step, the reaction solution was cooled to room temperature, and the resulting isupernatant was removed. The reddish residue was washed several times with isopropyl alcohol and twice with ether, followed by drying under reduced pressure to form 8.9 g of potassium salt of carboxyethyl indolenium sulfonate. The yield was 93%. Table 3 shows the structure of the potassium salt, chemical shifts of NMR in dimethylsulfoxide (DMSO) and assignment of each peak.

TABLE 3

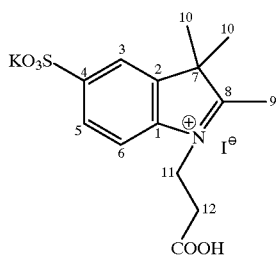

| Chemical Shift (δ, ppm) | Number of Hydrogen | Number of Peak | Assigned Carbon No. |
|---|---|---|---|
| 1.53 | 6 | 1 | 10 |
| 2.49 | 3 | 1 | 9 |
| 2.85 | 2 | m | 12 |
| 2.97 | 2 | 3 | 11 |
| 7.38 | 1 | 3 | 6 |
| 7.64 | 1 | m | 5 |
| 8.01 | 1 | 2 | 3 | m: many

④ Synthesis of Carboxylic Acid Derivative

Potassium salt of carboxyethyl indolenium sulfonate, 5 g (11 mmol), which was synthesized in the manner as described in the above item ③, was dissolved in 20 ml of pyridine. To the solution gradually was added 3.1 g (21 mmol) of ethyl orthoformate dropwise over 15 minutes while the mixture was being refluxed in argon flow. The reaction mixture was refluxed for 2 hours and cooled to room temperature. Ether (80 ml) was added to the reaction mixture to solidify, and the supernatant was removed. The resulting reddish brown solid was dissolved in 10 ml of ethanol. Ether (200 ml) was added to the solution to solidify again while stirring. The solid was collected by filtration and washed with ether, followed by drying under reduced pressure to form 2.5 g of a carboxylic acid derivative. The yield was 29%. Table 4 shows the structure of the carboxylic acid derivative, chemical shifts of NMR in dimethylsulfoxide (DMSO) and assignment of each peak.

TABLE 5

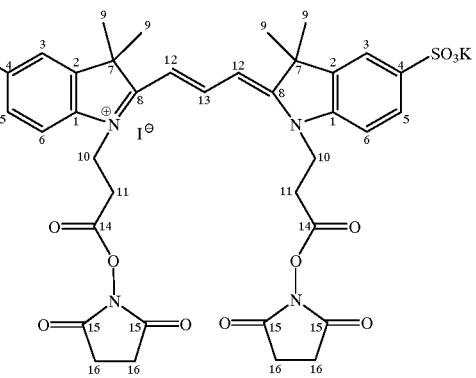

| Chemical Shift (δ, ppm) | Number of Hydrogen | Number of Peak | Assigned Carbon No. |
|---|---|---|---|
| 1.70 | 12 | 1 | 9 |
| 2.35 | 4 | m | 11 |
| 3.90 | 4 | m | 10 |
| 6.45 | 2 | 2 | 12 |
| 7.41 | 2 | 2 | 6 |
| 7.80 | 2 | m | 5 |
| 7.89 | 2 | 2 | 3 |
| 8.43 | 1 | m | 13 | m: many

⑤ Synthesis of Cyanine Dye

Carboxylic acid derivative, 1 g (1.2 mmol), which was synthesized in the manner as described in the above item ④, and hydroxysuccinimide 0.28 g (2.4 mmol) were dissolved in 20 ml of dimethylformamide. To the solution gradually was added 5 ml of dimethylformamide solution containing 0.49 g (2.4 mmol) of dicyclohexylcarbodiimide dropwise over 15 minutes while stirring at 0° C. The mixture was stirred at room temperature overnight. The resulting precipitate was eliminated by filtration. About 300 ml of ether was added to the filtrate. The resulting reddish brown solid was collected by filtration and washed twice with ether, followed by drying under reduced pressure to form 0.68 g of a cyanine dye represented by Formula I. The yield was 29%. The cyanine dye will be hereinafter referred to as "IC3-OSu". Table 5 shows the structure of IC3-OSu, chemical shifts of NMR in dimethylsulfoxide (DMSO) and assignment of each peak.

TABLE 4

| Chemical Shift (δ, ppm) | Number of Hydrogen | Number of Peak | Assigned Carbon No. |
|---|---|---|---|
| 1.75 | 12 | 1 | 9 |
| 1.99 | 8 | m | 16 |
| 2.40 | 4 | m | 11 |
| 3.95 | 4 | m | 10 |
| 6.42 | 2 | 2 | 12 |
| 7.45 | 2 | 2 | 6 |
| 7.83 | 2 | m | 5 |
| 7.92 | 2 | 2 | 3 |
| 8.43 | 1 | m | 13 | m: many (2) Polymerization of Mouse IgG

Mouse IgG, 10 mg ($6.667 \times 10^{-5}$ mmol) was dissolved in 1 ml of PBS. To the solution was added 0.1 ml of PBS solution containing 4.057 mg (0.006667 mmol, 100 equivalent) of DTSSP (produced by Pierce Chemical Company) while stirring at room temperature. After a 30-min stirring step at 35° C., a gel filtration was performed using a sephadex G25M column (produced by Pharmacia) to form about 6 ml of PBS solution of aggregate IgG (IgG agg.). The concentration of the obtained solution was determined as follows.

The absorbance at 280 nm was measured using 0.5 ml of the obtained solution and found to be 2.43. Since the observed absorbance at 280 nm was accounted for by IgG, the concentration of IgG [IgG agg.] was determined by Equation I provided that the molar extinction coefficient of IgG at 280 nm was $2.099 \times 10^5$.

$$[\text{IgG agg.}] = 2.43/2.099 \times 10^{-5} = 1.158 \times 10^5 (M) \qquad \text{Equation I}$$

(3) Dye-labeling of Antibody Conjugate

IC3-OSu, which was obtained in the manner as described in Item (1), was dissolved in 0.2 ml of PBS to prepare 27.5 mg of a dye solution. The dye solution will be hereinafter referred to as "SLIC3". SLIC3 was added dropwise to the IgG agg. solution obtained in the manner as described in Item (2). The mixture was allowed to stand at 4° C. for 20 hours and then dialyzed against 20 liters of PBS to eliminate unreacted dye molecules. About 6 ml of PBS solution of antibody conjugate was thus labeled with SLIC3.

The number of SLIC3 molecules per molecule of IgG in the obtained SLIC3-labeled antibody conjugate was determined as follows. The absorbances at 280 nm and 550 nm were first measured using the obtained solution and found to be 6.78 and 38.1, respectively. The observed absorbances are accounted for by SLIC3 because the antibody conjugate has no adsorption at 550 nm. Therefore, the concentration of SLIC3 [SLIC3] was determined by Equation II provided that the molar extinction coefficient of SLIC3 at 550 nm was $8.55 \times 10^4$.

$$[SLIC3] = 38.1/8.55 \times 10^4 = 4.46 \times 10^{-4} (M) \quad \text{Equation II}$$

Though the observed absorbance at 280 nm was indeed caused by the antibody conjugate, the actual concentration of the antibody conjugate [IgG agg.] was determined by taking into account an influence from the adsorption of SLIC3 at 280 nm. Consequently, the actual concentration of the antibody conjugate [IgG agg.] was determined by Equations III and IV provided that Ab280, IgG stands for the absorbance at 280 nm derived from the antibody conjugate, the molar extinction coefficient of SLIC3 at 280 nm was $9.8 \times 10^3$, and the molar extinction coefficient of the antibody conjugate at 280 nm was $2.099 \times 10^5$.

$$Ab280, IgG = 6.78 - (4.46 \times 10^{-4} \times 9.8 \times 10^3) = 2.41 \quad \text{Equation III}$$

$$[IgG\ agg.] = 2.41/2.099 \times 10^5 = 1.150 \times 10^{-5} (M) \quad \text{Equation IV}$$

Finally, the number of SLIC3 molecules bonding to each IgG molecule was determined by Equation V.

$$[SLIC3]/[IgG\ agg.] = 4.46 \times 10^{-4}/1.150 \times 10^{-5} = 25.8 (\text{molecules}) \quad \text{Equation V}$$

(4) Evaluation of Dye-labeled Mouse IgG Conjugate

The chromaticity (sensitivity) due to aggregation of the dye-labeled antibody conjugate was examined by measurement of the absorbance at 550 nm using the resulting dye-labeled mouse IgG conjugate for immunochromatographic sensors. As a comparative example, the chromaticity (sensitivity) due to aggregation of a dye-labeled antibody was similarly examined by measurement of the absorbance at 550 nm using a dye-labeled antibody which was prepared in the same manner as described above except for not polymerizing the antibody. As a result of the measurement, the absorbance of the dye-labeled antibody conjugate of the embodiment was found to be about 0.8. On the other hand, the absorbance of the dye-labeled antibody of the comparative example was found to be about 0.07. This leads to a conclusion that the dye-labeled antibody conjugate of the present invention shows a sensitivity about ten times as high as the sensitivity of the dye-labeled antibody of the comparative example. The configuration of the immunochromatographic sensor used and the measurement of the absorbance were as follows.

Configuration of Immunochromatographic Sensor

FIG. 1 shows an example of the immunochromatographic sensor. In immunochromatographic sensor 1, a first glass filter paper, antibody-immobilizing membrane 6 and second glass filter paper are disposed on supporting plate 2 in this order. Antibody-immobilizing membrane 6 is formed of nitrocellulose. Supporting plate 2 is formed of plastic such as polyvinylchloride. An end of the first glass filter paper with which antibody-immobilizing membrane 6 is not contacted is water-distribution part 3 (left end in FIG. 1). The end of the first glass filter paper with which antibody-immobilizing membrane 6 is contacted is labeled antibody part 4 where a dye-labeled antibody conjugate is impregnated. In the comparative example, labeled antibody part 4 is impregnated with a dye-labeled antibody which is not polymerized. Antibody immobilizing part 5 is provided at a predetermined position of antibody-immobilizing membrane 6 by adsorption. An antibody which is supposed to react with the same antigen as the dye-labeled antibody reacts with is immobilized at antibody immobilizing part 5. The second glass filter paper works as water-absorbing part 7.

Measurement of Absorbance

An example of measuring absorbance using sensor 1 is performed as follows. A sample such as urine is first applied to water-distribution part 3. Following the principle of chromatography, the sample moves toward water-absorbing part 7 in the direction indicated by arrow A in FIG. 1. While the sample is moving toward water-absorbing part 7, the labeled antibody bonds to the antigen contained in the sample at labeled antibody part 4. The antigen to which the labeled antibody has bonded and the sample move toward antibody immobilizing part 5, and the antigen bonds to the immobilized antibody and is immobilized there. Antibody immobilizing part 5 is irradiated with light L1 having a predetermined wavelength such as 550 nm. Absorbance is measured by measuring reflected light L2 of light L1.

As explained above, the dye-labeled antibody conjugate of the invention has more sensitivity because the antibody conjugate has many reactive sites to antigens. Therefore, introduction of the dye-labeled antibody conjugate of the invention in sensors using immunochromatography makes it possible to produce sensors more sensitive than those using labeled antibodies prepared in the conventional methods.

The invention may be embodied in other specific forms without departing from the spirit or essential characteristics thereof. The embodiments disclosed in this application are to be considered in all respects as illustrative and not restrictive, the scope of the invention being indicated by the appended claims rather than by the foregoing description, and all changes which come within the meaning and range of equivalency of the claims are intended to be embraced therein.

What is claimed is:

1. A dye-labeled antibody conjugate comprising an antibody conjugate and a cyanine dye, wherein said antibody conjugate comprises an antibody polymerized using a polyfunctional reagent, and said antibody conjugate is labeled with said cyanine dye.

2. The dye-labeled antibody conjugate according to claim 1, wherein said polyfunctional reagent is dithiobis (sulfosuccinimidylpropionate).

3. The dye-labeled antibody conjugate according to claim 1, wherein said cyanine dye is a cyanine dye having a chemical structure represented by Formula I Formula I

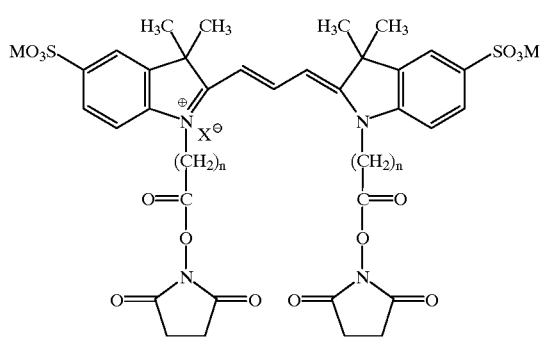

wherein X represents a halogen, M represents a hydrogen or alkali metal, and n represents an integer of 1 to 4.

4. The dye-labeled antibody conjugate according to claim 3, wherein said antibody conjugate is bonded to said cyanine dye via a covalent bond.

5. A method of preparing a dye-labeled antibody conjugate comprising the steps of polymerizing antibody using a polyfunctional reagent in the presence of a buffer having a pH value in a medium or slight alkaline region and adding a cyanine dye to the buffer in order to label the antibody polymerized.

6. The method according to claim 5, wherein said polyfunctional reagent is dithiobis (sulfosuccinimidylpropionate).

7. The method according to claim 5, wherein said cyanine dye is a cyanine dye having a chemical structure represented by Formula I Formula I

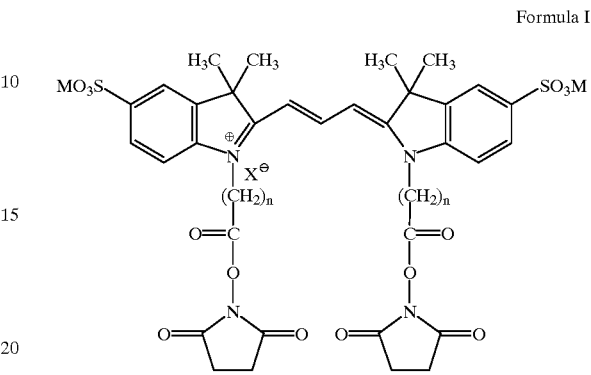

wherein X represents a halogen, M represents a hydrogen or alkali metal, and n represents an integer of 1 to 4.

8. The method according to claim 5, wherein said buffer is a phosphate buffer.

* * * * *